United States Patent
Domack (10) Patent No.: US 7,556,177 B2
(45) Date of Patent: Jul. 7, 2009

(54) SLIDE EJECTOR MECHANISM SUITABLE FOR USE IN A LABORATORY INSTRUMENT

(75) Inventor: Thomas E. Domack, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 625 days.

(21) Appl. No.: 11/087,893

(22) Filed: Mar. 23, 2005

(65) Prior Publication Data
US 2006/0213923 A1     Sep. 28, 2006

(51) Int. Cl.
*B65G 59/00*     (2006.01)
(52) U.S. Cl. .................. 221/272; 221/246; 221/255; 221/256; 221/261; 221/263; 221/265; 221/268; 221/270; 221/277
(58) Field of Classification Search .......... 221/270, 221/272, 277, 268, 265, 263, 261, 255, 256, 221/246, 274
See application file for complete search history.

(56) References Cited

U.S. PATENT DOCUMENTS

| | | | | |
|---|---|---|---|---|
| 3,040,617 A | * | 6/1962 | Rankin | 221/199 |
| 5,195,653 A | * | 3/1993 | Gerrans | 221/274 |
| 5,601,208 A | * | 2/1997 | Scott | 221/256 |
| 6,319,470 B1 | | 11/2001 | Lefevre et al. | |
| 6,796,455 B2 | * | 9/2004 | Schmidt | 221/256 |

* cited by examiner

*Primary Examiner*—Gene Crawford
*Assistant Examiner*—Timothy R Waggoner
(74) *Attorney, Agent, or Firm*—Sterne, Kessler, Goldstein & Fox P.L.L.C.

(57) ABSTRACT

A slide ejector mechanism for automatically removing a slide from a slide stack is set forth. The slide ejector mechanism comprises an ejector blade adapted to engage a longitudinal edge of the slide and an ejector drive. The ejector drive is connected to rotate the ejector blade through a curved ejection path. During this rotation, the ejector blade engages the longitudinal edge of the slide to remove the slide from the slide stack and place the slide at an output position for subsequent manipulation. In accordance with a further enhancement, the slide ejector mechanism may include structures that render the apparatus self-cleaning of broken slides. Such structures may include a platen having an opening therethrough along at least a portion of the ejection path. The opening has a width that is slightly less than a length of the slide so that the slide spans the opening and is supported at its edges by the platen.

26 Claims, 8 Drawing Sheets

SLIDE EJECTOR MECHANISM SUITABLE FOR USE IN A LABORATORY INSTRUMENT

FIELD OF THE INVENTION

The present invention is generally directed to an apparatus for manipulating an object in a laboratory instrument or the like. More particularly, the present invention includes a slide ejector mechanism suitable for use in such instruments.

BACKGROUND OF THE INVENTION

Various analytical instruments execute processes in which an amount of a sample material is placed on a slide for further processing or examination. Such slides include standard laboratory glass microscope slides. Typically, these standard slides are about 1"×3"×0.04" in size and are packaged in a box of 72 slides each. Three packages of these slides are normally stacked vertically on the instrument. The slides are then individually introduced to the instrument by removing a single slide from the bottom of the stack.

Removal of the slides from the bottom of the stack can be quite problematic. The friction caused by the weight of the slides in the stack and the vacuum created between the slides because of their smooth finish result in the bottom slide sticking to the slide immediately above it. This problem is exacerbated when an amount of moisture from condensation gets between the slide surfaces.

An apparatus having an extractor unit adapted to remove a slide from the bottom of a slide stack is illustrated in U.S. Pat. No. 6,319,470, entitled "Device for Automatic Preparation of Blood Smears on Plates" and issued to Lefevre et al. The slide extractor unit shown in the '470 patent includes a thruster having a blade that is displaced linearly in the direction of slide extraction. The slide stack is presented to the slide extractor unit at an angle so that the longitudinal edge of the slide engaged by the blade is at a slight angle relative to the direction of extraction. In accordance with one embodiment, the angle is 3°, such that the longitudinal edge of the slide forms an angle of 93° relative to the direction of extraction. According to the '470 patent, installing the stack of slides with angular offsetting of this type permits more efficient detachment of the slides and limits blockages or slowing down caused by slides adhering together.

Despite the purported mechanical advantage associated with the foregoing apparatus, a significant amount of force is still required to extract a slide from the bottom of a slide stack. The removal force is initially focused on only a small portion of the longitudinal edge of the bottom slide and can cause the slide to break. Still further, no provision is made for slides that break under this force. Additionally, implementation of the foregoing apparatus typically results in complex mechanisms that are difficult to build and service. The present inventor has recognized a need for an improved ejector apparatus that addresses many of these deficiencies.

SUMMARY OF THE INVENTION

A slide ejector mechanism for automatically removing a slide from a slide stack is set forth. The slide ejector mechanism comprises an ejector blade adapted to engage a longitudinal edge of the slide and an ejector drive. The ejector drive is connected to rotate the ejector blade through a curved ejection path. During this rotation, the ejector blade engages the longitudinal edge of the slide to remove the slide from the slide stack and place the slide at an output position for subsequent manipulation. In accordance with a further enhancement, the slide ejector mechanism may include structures that render the apparatus self-cleaning of broken slides. Such structures may include a platen having an opening therethrough along at least a portion of the ejection path. The opening has a width that is slightly less than a length of the slide so that the slide spans the opening and is supported at its edges by the platen.

DESCRIPTION OF A PREFERRED EMBODIMENT OF THE INVENTION

Figure 1:
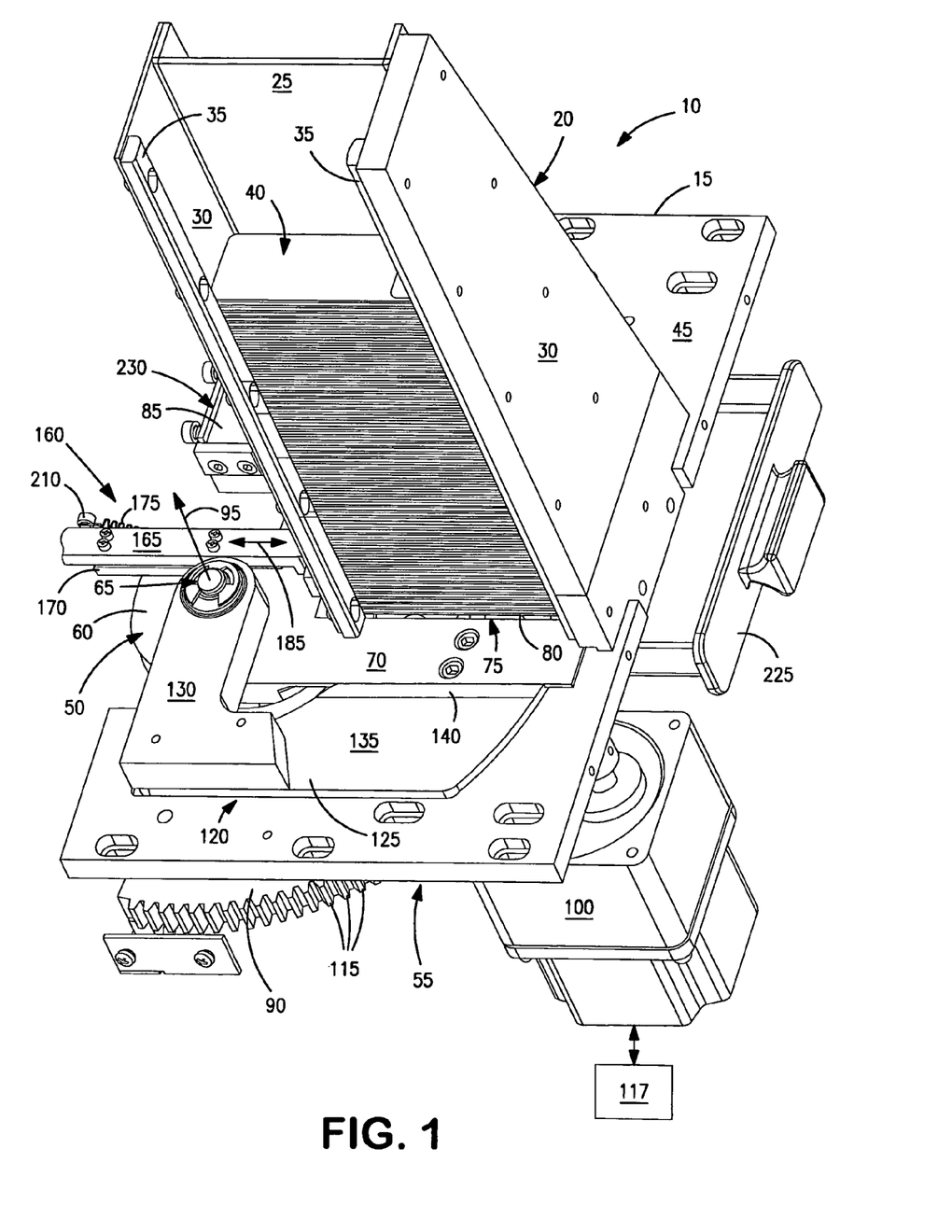
FIG. 1 is a perspective view of a slide ejector mechanism constructed in accordance with one embodiment of the present invention.

One embodiment of an ejector mechanism constructed in accordance with the teachings of the present invention is shown generally at 10 of FIG. 1. As illustrated, the ejector mechanism 10 includes a horizontally oriented platen 15 that supports a vertically oriented slide bin 20. In this embodiment, slide bin 20 includes a lateral wall 25 separating a pair of sidewalls 30. Guide rails 35 extend inward of sidewalls 30. Lateral wall 25, sidewalls 30 and guide rails 35 are arranged to generally conform to the exterior edges of a stack of slides 40. The bottom of stack 40 is engaged by a support surface 45 of the platen 15. Lateral wall 25 includes an outlet opening at the bottom thereof that is large enough to allow removal of at least one slide from the bottom of slide stack 40.

Ejector mechanism 10 also comprises an ejector blade 50 and an ejector drive shown generally 55. Ejector blade 50 includes a mounting portion 60 that is secured to platen 15 at a pivot joint 65, and a rectangular portion 70 having an edge 75 adapted to engage a longitudinal edge 80 of a single slide at the bottom of slide stack 40.

Ejector drive 55 is connected to rotate the ejector blade 50 through a curved ejection path of the pivot joint 65. Preferably, without limitation, the curved ejection path is arcuate and will be described as such in connection with the illustrated embodiment. In accordance with this motion, the edge 75 of the ejector blade 50 engages the longitudinal edge 80 of the bottom slide to rotatably displace the slide from stack 40 and ultimately position it at an output position 85 for subsequent manipulation. Preferably, edge 75 is generally continuous in its engagement with longitudinal edge 80 to effectively reduce the amount of force per unit area applied to the slide edge and thereby diminish the likelihood of breakage. However, discontinuous engagement between edges 75 and 80 may likewise be employed.

The ejector drive 55 may be constructed in a variety of different manners to impart the desired motion to the ejector blade 50. As can be seen from the top plan views of the apparatus shown in FIGS. 2B, 3B and 4 as well as the perspective view of the apparatus shown in FIGS. 1, 2A, and 3A the ejector drive 55 includes a segment gear 90 that has an axis of rotation 95 that is coincident with the pivot joint 65. The ejector blade 50 is fixed for co-rotation with the segment gear 90 about rotation axis 95. This segment gear 90 is rotated by a motor 100 having a drive shaft 105 that is connected to a pinion gear 110 that meshes with the teeth 115 at the periphery of the segment gear 90. Preferably, motor 100 is a rotating stepper motor that, for example, may be controlled by a programmable controller or similar control system 117.

Figure 5A:
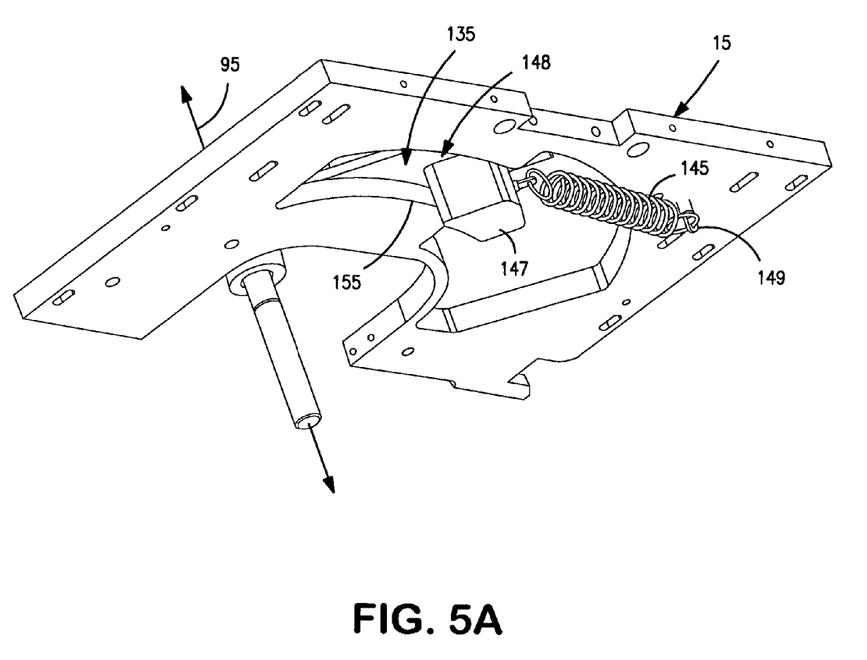
FIGS. 5A and 5B are bottom and top perspective views of the apparatus shown in FIG. 1 in which certain elements of the apparatus have been removed to expose various components used in the operation of the retaining blade assembly.
Figure 5B:
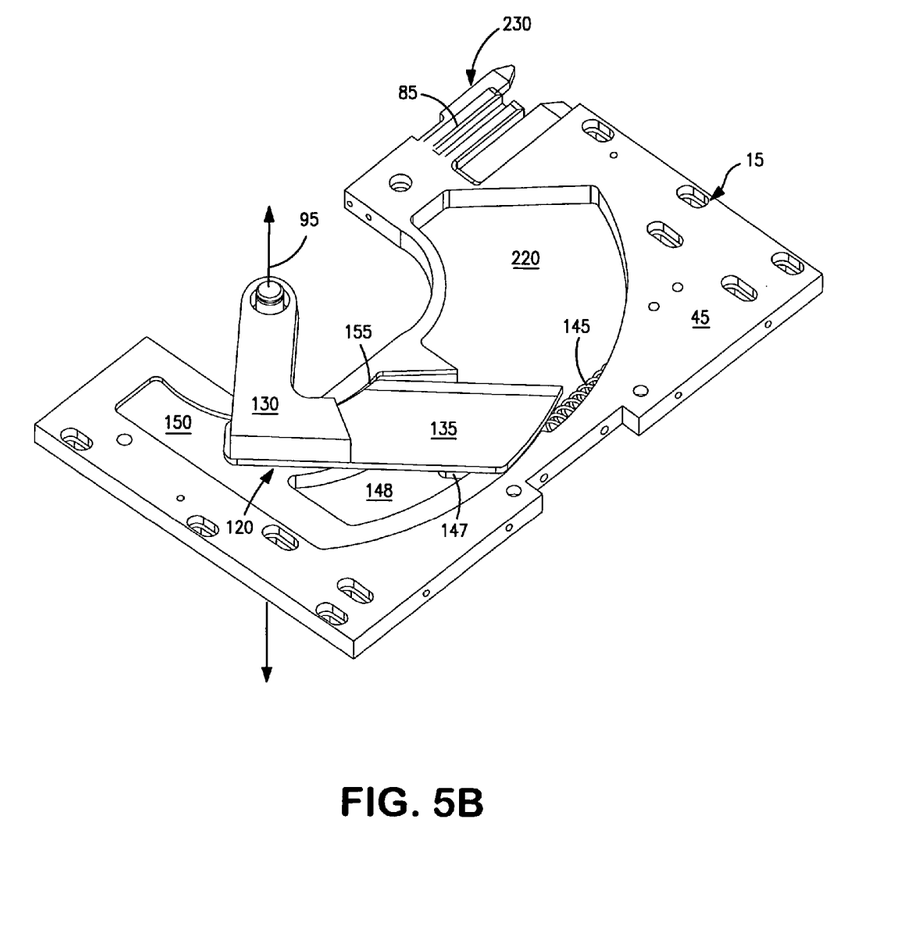

A retaining blade assembly, shown generally at 120, is also employed in the illustrated embodiment. In accordance with this embodiment, the retaining blade assembly 120 includes a retaining blade 125 having a mounting portion 130 that is secured to pivot joint 65 for rotation about axis 95. Retaining blade 125 also includes a blade portion 135 having a tapered edge 140. As illustrated in the simplified perspective views of the apparatus shown in FIGS. 5A and 5B. A bias member 145, such as a spring, is connected between an extension block 147 at the underside of blade portion 135 and a mounting nubbin 149 at the underside of platen 15 to provide the force necessary to rotate the blade portion 135 behind ejector blade 50. Blade portion 135 rotates behind ejector blade 50 as ejector blade 50 is driven to remove a slide from the bottom of slide stack 40. The bias member 145 also provides additional force through blade portion 135 to ejector blade 50 in its travel and gives a mechanical advantage to the overall assembly that reduces the drive requirements of motor 100. Extension block 147 extends through an arcuate guide channel 148 to facilitate proper positioning of the blade portion 135 as it follows the ejector blade 50.

Blade portion 135 only follows the ejector blade 50 through a portion of the arcuate ejection path. To this end, the range of motion of blade portion 135 is limited by a mechanical stop. In the illustrated embodiment, the mechanical stop is in the form of an edge 155 of a guide groove 150 disposed partially through the surface of platen 15 that restricts the travel of retaining blade assembly 120. Edge 155 engages retaining blade assembly 120 so that the motion of blade portion 135 is stopped once it is beneath slide stack 40. As such, blade portion 135 prevents the slides of slide stack 40 from moving downward as ejector blade 50 removes the bottommost slide.

After the ejector blade 50 has been driven to the end of the arcuate ejection path, motor 100 is operated to drive segment gear 90 so that the motion of ejector blade 50 is reversed along the path. The ejector blade 50 is thus driven into reverse contact with blade portion 135 thereby rotating retaining blade 125 about axis 95 against the bias of spring 145. The ejector blade 50 continues on this return path against retaining blade 125 until edge 75 lies behind slide stack 40. At this point, another slide is gravity fed and presented at the bottom of slide stack 40 for removal.

The illustrated embodiment also employs a lateral positioning mechanism, shown generally at 160. The lateral position mechanism 160 operates as a guide that contacts a transverse edge of the slide as the ejector blade 50 drives the slide along the arcuate ejection path. The particular embodiment of the lateral positioning mechanism 160 shown here includes a cam follower arm 165, a cam roller 167, a follower support 170 and a biasing member 175.

Follower support 170 is fixed to an upper surface of mounting portion 60 of ejector blade 50. Cam follower arm 165 is joined with follower support 170 in a manner that allows linear movement of the arm 165 along with roller 167 in the direction of arrows 180.

The upper portion of cam roller 167 engages a transverse edge 185 of a slide to guide the slide laterally as the ejector blade 50 moves it along the arcuate ejection path while the lower portion of cam roller 167 contacts camming surface 200. In the illustrated embodiment, camming surface 200 is formed from a contoured edge of platen 15. A biasing member 205, such as a spring, extends between connection nubbins 210 and 215 disposed on the follower arm 165 and ejector blade 50, respectively. Spring 205 thus drives cam roller 167 against camming surface 200 as ejector blade 50 is rotated along the arcuate ejection path. This places the cam roller 167 in the proper position to guide the slide laterally along the arcuate ejection path. Still further, the clockwise rotation of cam roller 167 as it moves along surface 200 drives the transverse edge 185 of slide 40 against edge 75 of ejector arm 70 thereby further enhancing the proper positioning and holding of slide 40 as it travels along the arcuate ejection path. In the illustrated embodiment, ejector blade 50 drives slide 40 toward the lateral positioning mechanism 160 and, as such, a further guide is not necessary on the side of slide 40 opposite mechanism 160.

The illustrated embodiment also includes structures that render the apparatus self-cleaning so that slide fragments are automatically removed from the ejection path in the event that a slide breaks during operation of the device. In this regard, platen 15 includes an opening 220 therethrough along at least a portion of the ejection path. The opening 220 has a width that is slightly less than a length of a slide so that an unbroken slide spans the opening 220 and is supported by the platen 15 at the slide edges. Broken slides, on the other hand, pass through opening 220 as ejector blade 50 is operated. A refuse container 225 is disposed below the opening 220 to receive any broken slide fragments. Preferably, refuse container 225 may be easily detached from mechanism 10 so that the slide fragments may be removed. Although the self-cleaning aspects shown herein are particularly suitable for use apparatus having an arcuate ejection path, it will be recognized that such self-cleaning aspects may likewise be incorporated in apparatus having linear or other shaped ejection paths.

Figure 2A:
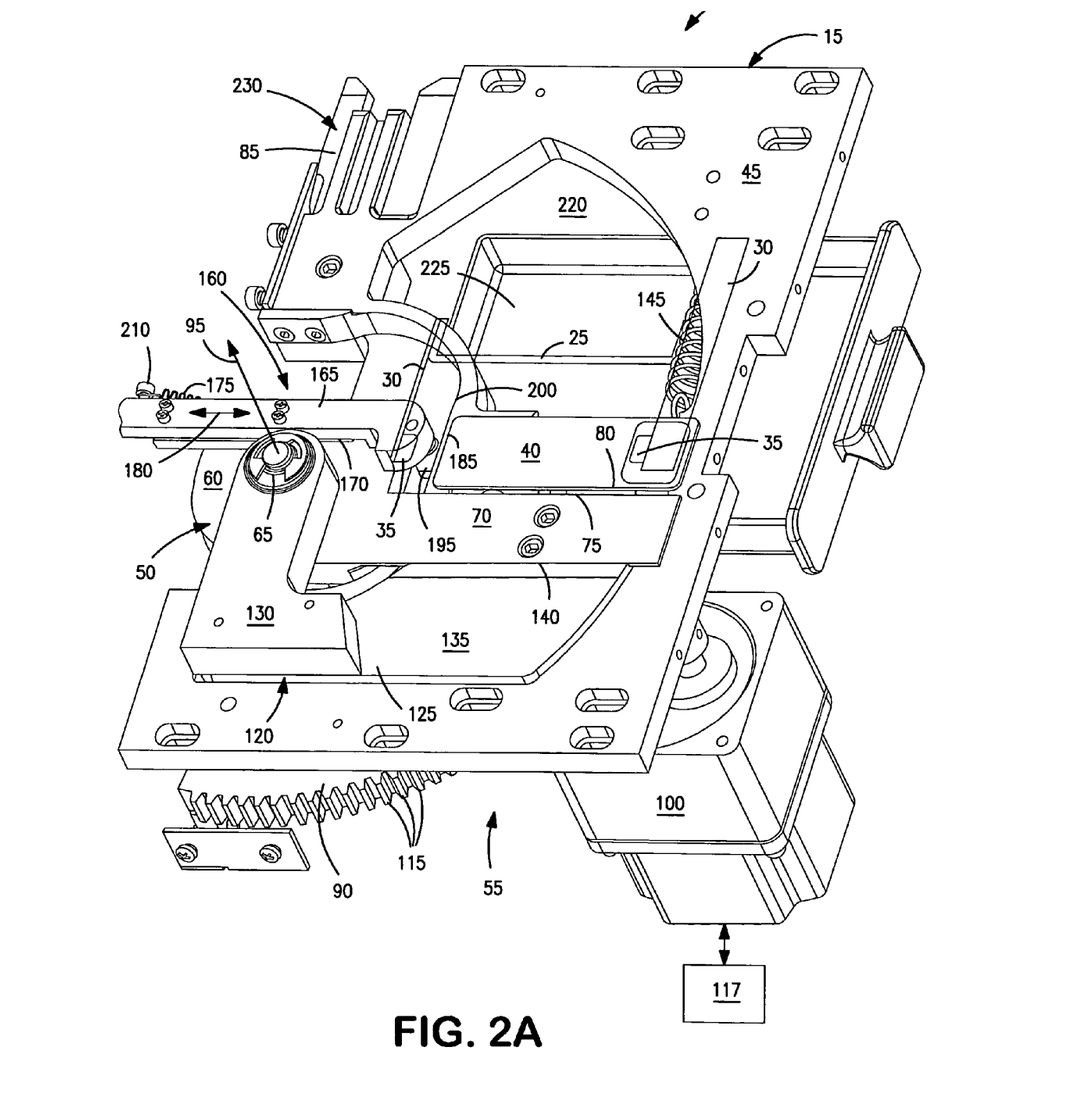
FIGS. 2A and 2B are perspective and top plan views, respectively, of the apparatus of FIG. 1 in an initial state in which it is ready to eject a slide from the slide stack.
Figure 2B:
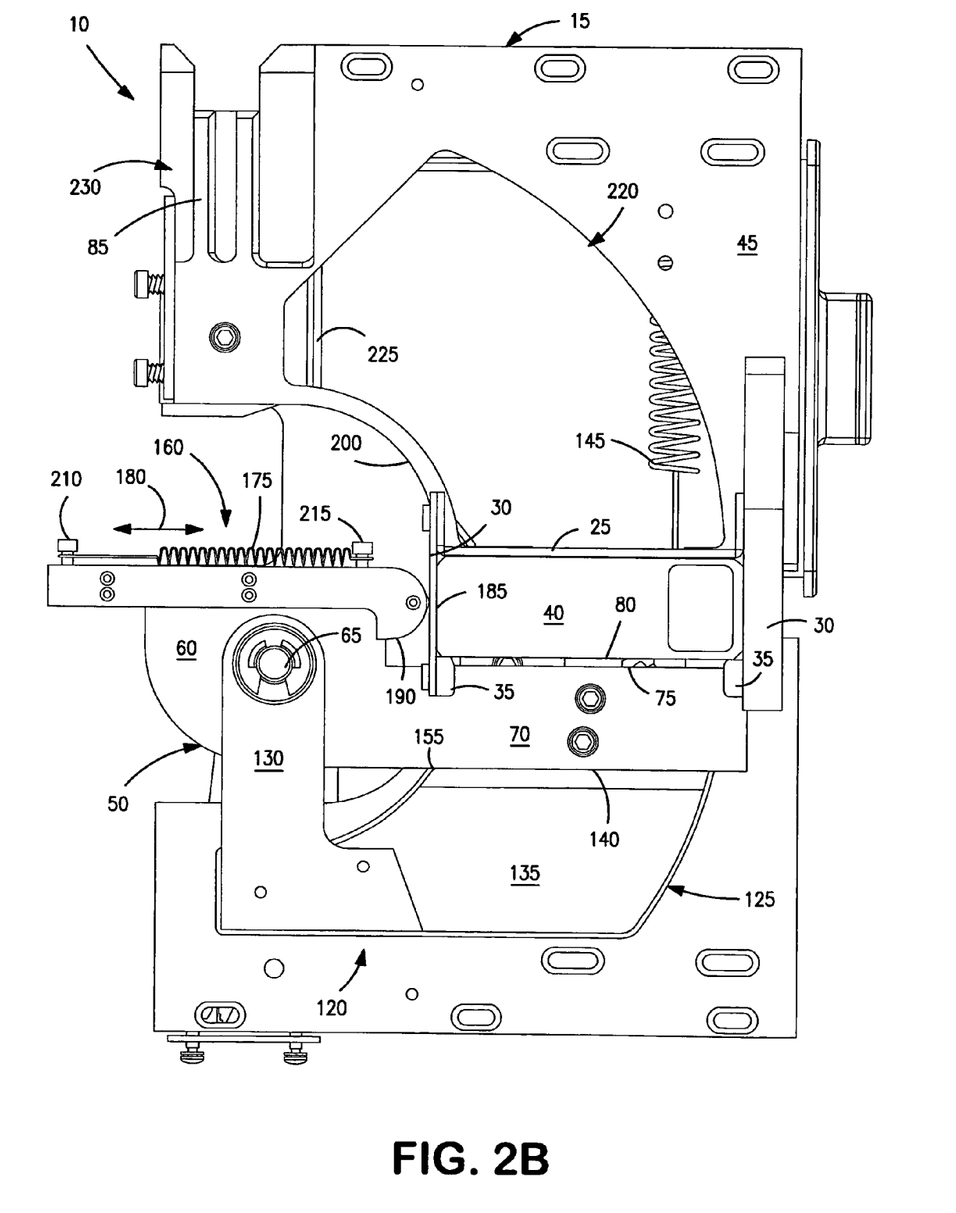

FIGS. 2A and 2B are perspective and top plan views, respectively, of the apparatus 10 in an initial state in which it is ready to eject a slide from slide stack 40. To simplify the drawings, only the bottommost slide of slide stack 40 is illustrated. As shown, ejector blade 50 has been driven against edge 140 of retaining blade 125 and in opposition to the force of spring 145. Edge 75 of ejector blade 50 is positioned for engagement with the longitudinal edge 80 of the bottom slide of stack 40. The cam roller 167 and camming surface 200 engage one another so that the cam roller 167 is disposed exterior of sidewall 30 of slide bin 20.

Figure 3A:
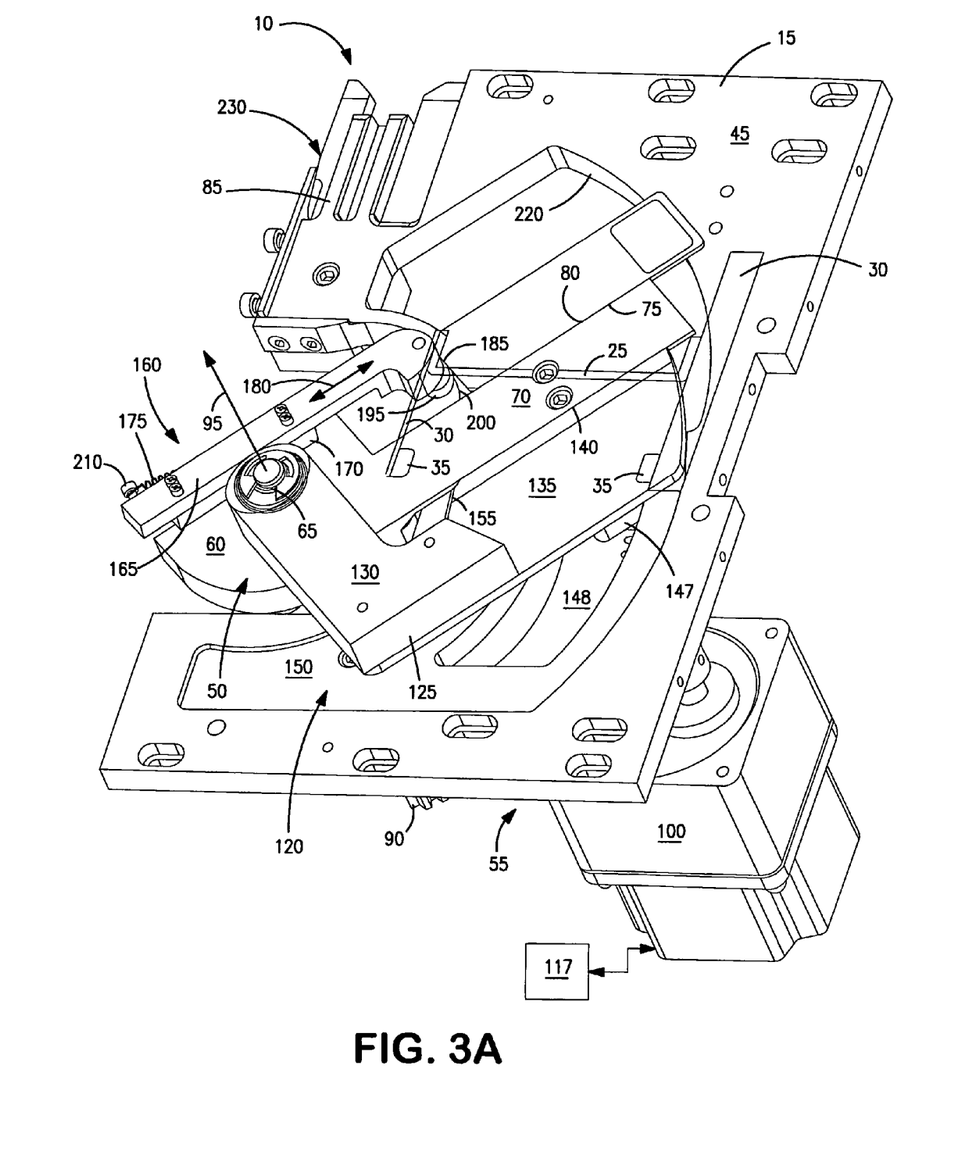
FIGS. 3A and 3B are perspective and top plan views, respectively, of the apparatus of FIG. 1 in an intermediate state in which a slide has just been removed from the slide stack.
Figure 3B:
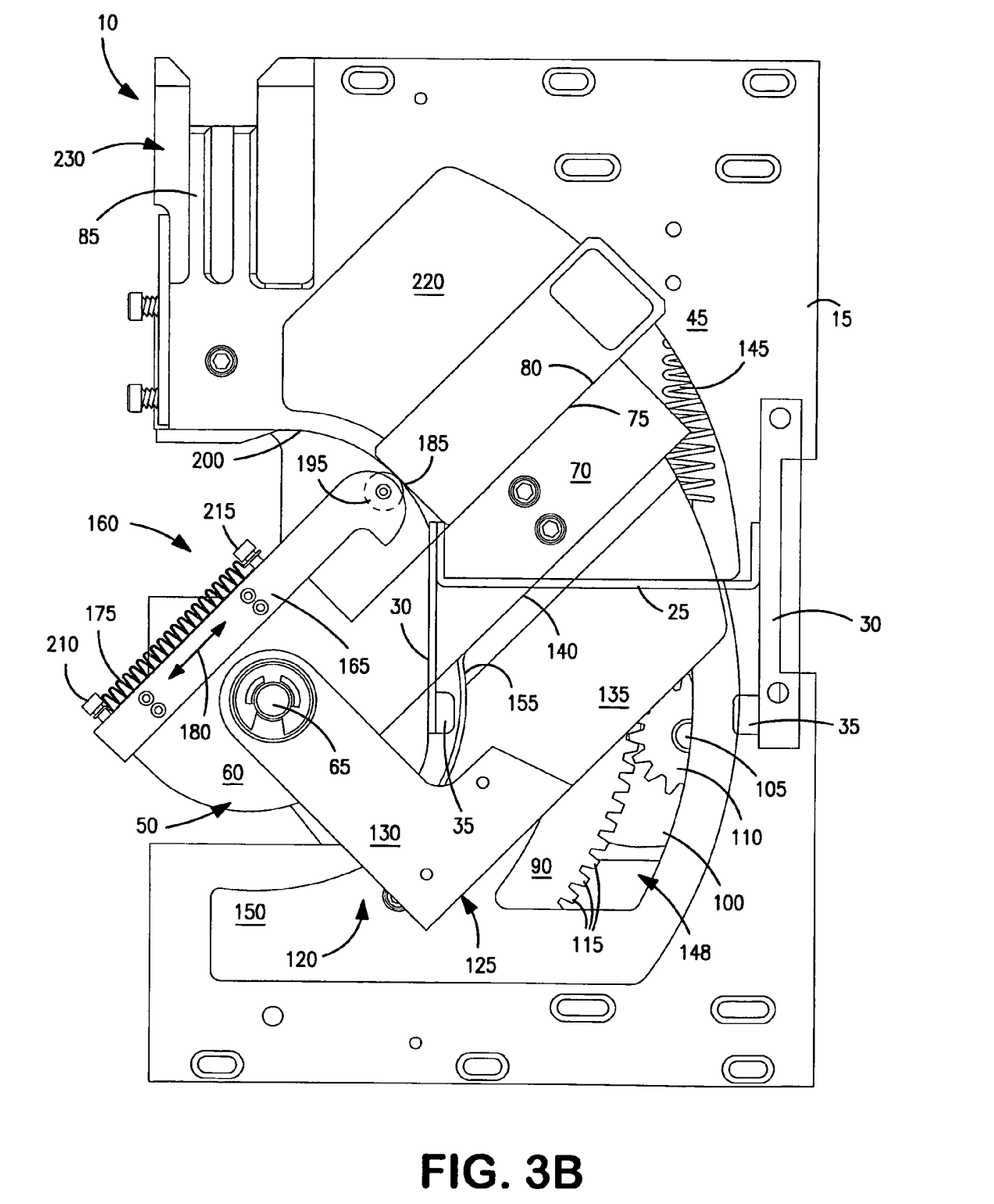

FIGS. 3A and 3B are perspective and top plan views, respectively, of the apparatus 10 in an intermediate state in which a slide has just been removed from slide stack 40. As shown, ejector drive 55 has driven edge 75 of ejector blade 50 against the longitudinal edge 80 of the slide and moved the slide along a portion of the arcuate ejection path. Retaining blade 125 has rotated with ejector blade 50 under the force of spring 145 and is positioned beneath the remaining slides of stack 40. The cam roller 167 and camming surface 200 have engaged one another so that the upper portion of cam roller 167 is disposed against the transverse edge 185 of the slide.

Figure 4:
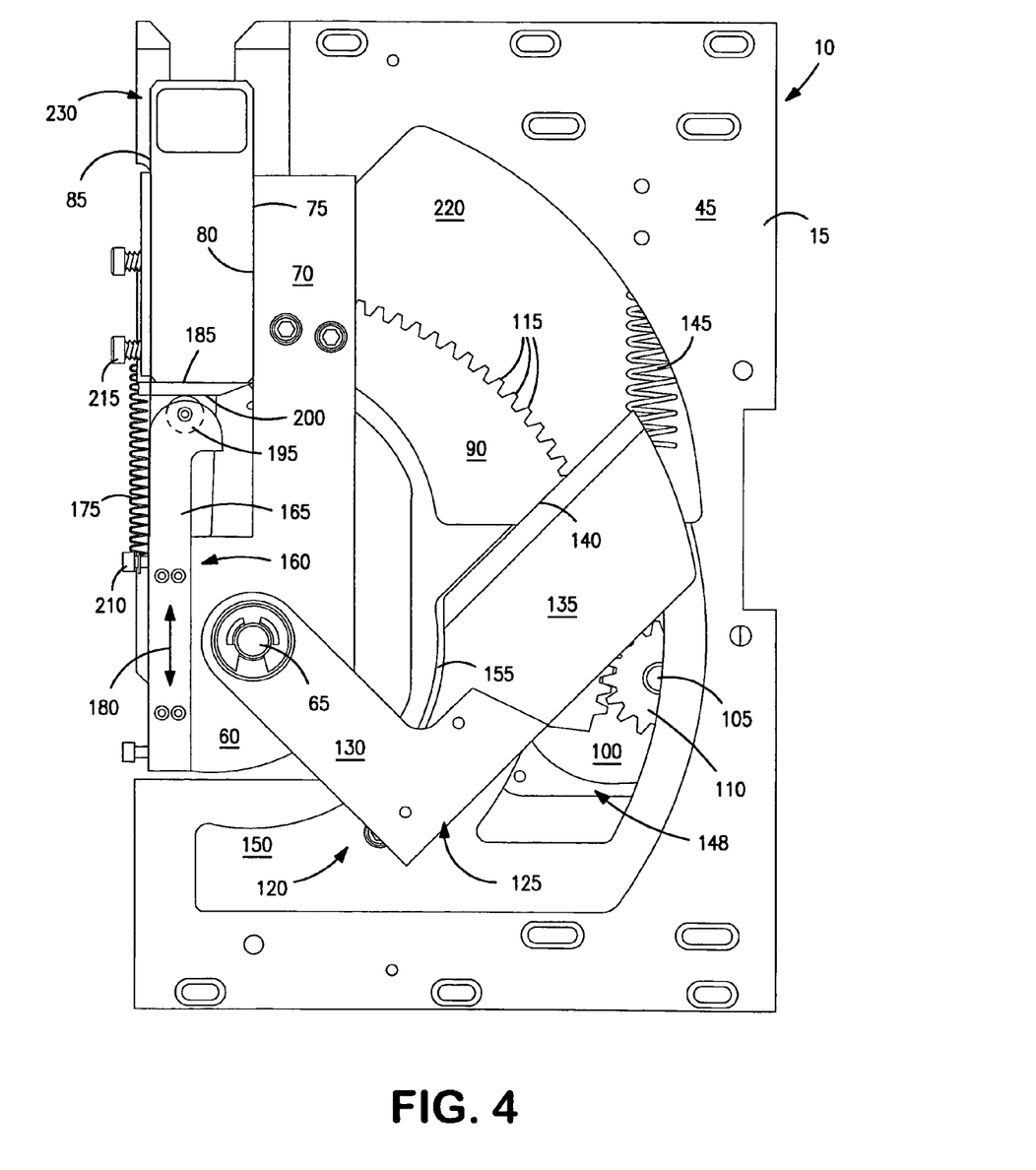
FIG. 4 is a top plan view of the apparatus of FIG. 1 in a final state in which the slide is presented on an output carriage for further manipulation.

FIG. 4 is a top plan view of the apparatus 10 in a final state in which the slide is presented for further manipulation. As shown, ejector drive 55 has driven edge 75 of ejector blade 50 against the longitudinal edge 80 of the slide and moved the slide to its final position along the arcuate ejection path. In this position, the slide has been received on an output carriage 230. Retaining blade assembly 120 has now engaged edge 155 of guide groove 150 so that retaining blade 125 can no longer rotate with ejector blade 50 under the force of spring 145. Rather, retaining blade 125 remains in position beneath the remaining slides of stack 40. Cam roller 167 and camming surface 200 have continued to engage one another so that the upper portion of cam roller 167 has guided the transverse edge 185 of the slide into position and is now disengaged from it.

Numerous modifications may be made to the foregoing system without departing from the basic teachings thereof. Although the present invention has been described in substantial detail with reference to one or more specific embodiments, those of skill in the art will recognize that changes may be made thereto without departing from the scope and spirit of the invention as set forth in the appended claims.

What is claimed is:

1. A slide ejector mechanism comprising:
   an ejector blade adapted to engage a longitudinal edge of a slide;
   an ejector drive connected to rotate said ejector blade through an ejection path whereby said ejector blade engages said longitudinal edge of said slide to move said slide along the ejection path to an output position;
   a platen upon which the slide is moved by the ejector blade along the ejection path; and
   a drive motor coupled to the ejector drive and configured to rotate the ejector drive.

2. A slide ejector mechanism as claimed in claim 1 wherein the ejection path is arcuate.

3. A slide ejector mechanism as claimed in claim 1 wherein the platen includes an opening disposed along at least a portion of the ejection path; and
   a refuse container disposed below said platen opening.

4. A slide ejector mechanism as claimed in claim 3 wherein said refuse container is removable.

5. A slide ejector mechanism as claimed in claim 1 and further comprising:
   a retaining blade adapted to follow said ejector blade along at least a portion of the ejection path.

6. A slide ejector mechanism as claimed in claim 1 and further comprising a lateral positioning mechanism adapted to engage a transverse edge of said slide as said slide is driven by said ejector blade along the ejection path.

7. A slide ejector mechanism as claimed in claim 6 wherein said lateral positioning mechanism comprises comprising:
   a camming surface;
   a cam follower arm having a roller, said roller having a first surface engaging said camming surface and a second surface adapted to engage a transverse edge of said slide as said ejector blade drives said slide along the ejection path;
   a cam follower support coupled to said ejector blade, said cam follower arm being joined to said cam follower support so as to allow linear movement therebetween; and
   a biasing member disposed to drive said roller of said cam follower arm against said camming surface along said cam follower support.

8. A slide ejector mechanism comprising:
   an ejector blade adapted to engage an edge of a slide;
   an ejector drive connected to rotate the ejector blade through an ejection path whereby the ejector blade engages the edge of the slide to remove the slide from a slide stack and place the slide at an output position;
   a drive motor configured to rotate the ejector drive; and
   a segment gear disposed for rotation about a rotation axis, said ejector blade being in alignment with said segment gear for rotation about said rotation axis; and
   a pinion gear disposed on a rotatable drive shaft of the drive motor and engaging said segment gear.

9. A slide ejector mechanism as claimed in claim 8 wherein said drive motor is a rotary stepper motor.

10. A slide ejector mechanism as claimed in claim 9 and further comprising a programmable control system connected to control said rotary stepper motor.

11. A slide ejector mechanism comprising:
    a platen having an opening therethrough along at least a portion of a curved ejection path;
    an ejector blade adapted to engage a longitudinal edge of said slide;
    an ejector drive connected to rotate said ejector blade through said curved ejection path on said platen whereby said ejector blade engages said longitudinal edge of said slide to remove said slide from said slide stack and place said slide at an output position; and
    a lateral positioning mechanism adapted to engage a transverse edge of said slide as said slide is driven by said ejector blade along said curved ejection path to thereby guide said slide radially along said curved ejection path.

12. A slide ejector mechanism as claimed in claim 11 wherein said curved ejection path is arcuate.

13. A slide ejector mechanism as claimed in claim 11 and further comprising a retaining blade adapted to follow said ejector blade along at least a portion of said curved ejection path.

14. A slide ejector mechanism as claimed in claim 11 and further comprising a refuse container disposed below said opening of said platen.

15. A slide ejector mechanism as claimed in claim 11 wherein said lateral positioning mechanism comprises:
    a camming surface;
    a cam follower arm having a roller, said roller having a first surface engaging said camming surface and a second surface adapted to engage a transverse edge of said slide as said ejector blade drives said slide along said curved ejection path;
    a cam follower support coupled to said ejector blade, said cam follower arm being joined to said cam follower support so as to allow linear movement therebetween; and
    a biasing member disposed to drive said roller of said cam follower arm against said camming surface along said cam follower support.

16. A slide ejector mechanism as claimed in claim 11 wherein said ejector drive comprises:
    a segment gear disposed for rotation about a rotation axis, said ejector blade being in fixed alignment with said segment gear for rotation about said rotation axis;
    a drive motor having a rotatable drive shaft; and
    a pinion gear disposed on said rotatable drive shaft and engaging said segment gear.

17. A slide ejector mechanism as claimed in claim 16 wherein said drive motor is a rotary stepper motor.

18. A slide ejector mechanism as claimed in claim 17 and further comprising a programmable control system connected to control said rotary stepper motor.

19. A slide ejector mechanism comprising:
    a platen having an opening therethrough along at least a portion of an ejection path;
    an ejector blade adapted to engage a longitudinal edge of said slide;

an ejector drive connected to drive said ejector blade through said ejection path on said platen whereby said ejector blade engages said longitudinal edge of said slide to remove said slide from said slide stack and place said slide at an output position; and a retaining blade adapted to follow said ejector blade along at least a portion of said ejection path.

20. A slide ejector mechanism as claimed in claim 19 and further comprising a lateral positioning mechanism adapted to engage a transverse edge of said slide as said slide is driven by said ejector blade along said ejection path to thereby guide said slide laterally along said ejection path.

21. A slide ejector mechanism comprising:

a platen having an opening therethrough along at least a portion of an ejection path;

an ejector blade adapted to engage a longitudinal edge of said slide;

an ejector drive connected to drive said ejector blade through said ejection path on said platen whereby said ejector blade engages said longitudinal edge of said slide to remove said slide from said slide stack and place said slide at an output position; and a refuse container disposed below said opening of said platen.

22. A slide ejector mechanism as claimed in claim 21 wherein said refuse container is removable.

23. A slide ejector mechanism comprising:

a platen having an arcuate opening therethrough along at least a portion of an arcuate ejection path, said arcuate opening having a width that is less than a length of said slide;

an ejector blade adapted to engage a longitudinal edge of said slide;

an ejector drive connected to rotate said ejector blade through said arcuate ejection path on said platen whereby said ejector blade engages said longitudinal edge of said slide to remove said slide from said slide stack and place said slide at an output position; and a lateral positioning mechanism adapted to engage a transverse edge of said slide as said slide is driven by said ejector blade along said arcuate ejection path to thereby guide said slide radially along said curved ejection path.

24. A slide ejector mechanism as claimed in claim 23 and further comprising a retaining blade adapted to follow said ejector blade along at least a portion of said arcuate ejection path.

25. A slide ejector mechanism as claimed in claim 23 and further comprising a refuse container disposed below said arcuate opening of said platen.

26. A slide ejector mechanism as claimed in claim 23 wherein said lateral positioning mechanism comprises:

a camming surface;

a cam follower arm having a roller, said roller having a first surface engaging said camming surface and a second surface adapted to engage a transverse edge of said slide as said ejector blade drives said slide along said arcuate ejection path;

a cam follower support coupled to said ejector blade, said cam follower arm being joined to said cam follower support so as to allow linear movement therebetween; and a biasing member disposed to drive said roller of said cam follower arm against said camming surface along said cam follower support.

* * * * *